(12) United States Patent
King et al.

(10) Patent No.: US 11,998,576 B2
(45) Date of Patent: Jun. 4, 2024

(54) DIRECT-FED MICROBIALS

(71) Applicants: MICROBIAL DISCOVERY GROUP, LLC, Franklin, WI (US); UNITED ANIMAL HEALTH, INC., Sheridan, IN (US)

(72) Inventors: Michael R. King, Oak Creek, WI (US); Sona Son, Cudahy, WI (US); Kyle Leistikow, Franklin, WI (US); Nathan Robert Augspurger, Noblesville, IN (US)

(73) Assignees: MICROBIAL DISCOVERY GROUP, LLC, Franklin, IN (US); UNITED ANIMAL HEALTH, INC., Sheridan, IN (US)

( * ) Notice: Subject to any disclaimer, the term of this patent is extended or adjusted under 35 U.S.C. 154(b) by 0 days.

(21) Appl. No.: 17/403,284

(22) Filed: Aug. 16, 2021

(65) Prior Publication Data
US 2022/0241352 A1  Aug. 4, 2022

Related U.S. Application Data

(60) Division of application No. 16/454,593, filed on Jun. 27, 2019, now Pat. No. 11,110,134, which is a continuation of application No. 15/445,193, filed on Feb. 28, 2017, now Pat. No. 10,335,440.

(60) Provisional application No. 62/364,271, filed on Jul. 19, 2016, provisional application No. 62/301,438, filed on Feb. 29, 2016.

(51) Int. Cl.
| | |
|---|---|
| A61K 35/742 | (2015.01) |
| A23K 10/18 | (2016.01) |
| A23K 20/10 | (2016.01) |
| A23K 20/195 | (2016.01) |
| A23K 50/30 | (2016.01) |
| A23K 50/75 | (2016.01) |
| A61K 35/74 | (2015.01) |
| A61K 38/43 | (2006.01) |
| A61K 45/06 | (2006.01) |

(52) U.S. Cl.
CPC ............ *A61K 35/742* (2013.01); *A23K 10/18* (2016.05); *A23K 20/10* (2016.05); *A23K 20/195* (2016.05); *A23K 50/30* (2016.05); *A23K 50/75* (2016.05); *A61K 35/74* (2013.01); *A61K 38/43* (2013.01); *A61K 45/06* (2013.01)

(58) Field of Classification Search
CPC ...... A61K 35/742; A61K 35/74; A61K 38/43; A61K 45/06; A23K 10/18; A23K 20/10; A23K 20/195; A23K 50/30; A23K 50/75; A61P 31/04
See application file for complete search history.

(56) References Cited

U.S. PATENT DOCUMENTS

| | | | |
|---|---|---|---|
| 4,673,638 | A | 6/1987 | Grosch et al. |
| 5,587,475 | A | 12/1996 | Helquist et al. |
| 5,589,381 | A | 12/1996 | Neyra et al. |
| 5,665,354 | A | 9/1997 | Neyra et al. |
| 6,268,147 | B1 | 7/2001 | Beattie et al. |
| 7,754,469 | B2 | 7/2010 | Baltzley et al. |
| 7,807,185 | B2 | 10/2010 | Farmer |
| 8,025,874 | B2 | 9/2011 | Bellot et al. |
| 8,540,981 | B1 | 9/2013 | Wehnes et al. |
| 9,175,258 | B2 | 11/2015 | Bywater-Ekegard et al. |
| 9,410,213 | B2 | 8/2016 | Matheny et al. |
| 9,758,414 | B2 | 9/2017 | Dash et al. |
| 10,961,275 | B2 | 3/2021 | Bralkowski et al. |
| 2001/0027947 | A1 | 10/2001 | Tsuchiya |
| 2005/0255092 | A1 | 11/2005 | Rehberger et al. |
| 2005/0266468 | A1 | 12/2005 | Bedyzk et al. |
| 2006/0188978 | A1 | 8/2006 | Grant |
| 2008/0050774 | A1 | 2/2008 | Berka et al. |
| 2009/0280090 | A1 | 11/2009 | Rehberger et al. |
| 2010/0010080 | A1 | 1/2010 | Mockett et al. |
| 2010/0062021 | A1 | 3/2010 | Winkelman |
| 2010/0092428 | A1 | 4/2010 | Schmidt et al. |
| 2010/0291564 | A1 | 11/2010 | Stanley et al. |
| 2012/0100118 | A1 | 4/2012 | Rehberger et al. |
| 2012/0315258 | A1 | 12/2012 | Rehberger et al. |
| 2012/0315259 | A1 | 12/2012 | Friedlander |
| 2013/0064927 | A1 | 3/2013 | Davis et al. |
| 2013/0098837 | A1 | 4/2013 | Dash et al. |
| 2013/0100118 | A1 | 4/2013 | Mlyniec et al. |
| 2013/0136695 | A1 | 5/2013 | Hargis et al. |
| 2013/0216586 | A1 | 8/2013 | LeBrun et al. |

(Continued)

FOREIGN PATENT DOCUMENTS

| | | |
|---|---|---|
| CN | 101159102 A | 4/2008 |
| CN | 102223809 A | 10/2011 |

(Continued)

OTHER PUBLICATIONS

International search report and written opinion for PCT/US2017/019941, mailed May 26, 2017.

(Continued)

*Primary Examiner* — Jana A Hines
(74) *Attorney, Agent, or Firm* — Barnes & Thornburg LLP

(57) ABSTRACT

The invention relates to direct-fed microbials for use in *E. coli* inhibition in animals. More particularly, the invention relates to isolated *Bacillus* strains 101, 235, 77, 177, and 102 and strains having all of the identifying characteristics of these strains, for a use comprising the above-mentioned use. The invention can also be used for treatment of plants and in food processing.

16 Claims, No Drawings

(56) References Cited

U.S. PATENT DOCUMENTS

| | | | |
|---|---|---|---|
| 2013/0295067 | A1 | 11/2013 | Baltzley et al. |
| 2014/0106974 | A1 | 4/2014 | Sun et al. |
| 2014/0141044 | A1 | 5/2014 | Bhatt et al. |
| 2014/0273150 | A1 | 9/2014 | Angel |
| 2014/0315716 | A1 | 10/2014 | Matheny et al. |
| 2014/0363819 | A1 | 12/2014 | Rowlyk et al. |
| 2015/0079058 | A1 | 3/2015 | Nielsen et al. |
| 2015/0111214 | A1 | 4/2015 | Liu |
| 2015/0147303 | A1 | 5/2015 | Hsieh |
| 2015/0216203 | A1 | 8/2015 | Isaksen et al. |
| 2015/0216916 | A1 | 8/2015 | Galbraith et al. |
| 2016/0108467 | A1 | 4/2016 | Semikhodskii |
| 2017/0079308 | A1 | 3/2017 | King et al. |
| 2017/0166466 | A1 | 6/2017 | King et al. |
| 2017/0246224 | A1* | 8/2017 | King ..................... A61K 38/43 |
| 2017/0327840 | A1 | 11/2017 | Kijlstra et al. |
| 2018/0361444 | A1 | 12/2018 | Franssen et al. |
| 2019/0021341 | A1 | 1/2019 | Davis et al. |
| 2020/0015497 | A1 | 1/2020 | King et al. |
| 2020/0029592 | A1 | 1/2020 | King et al. |
| 2020/0093158 | A1 | 3/2020 | Calabotta et al. |

FOREIGN PATENT DOCUMENTS

| | | |
|---|---|---|
| CN | 103980535 A | 8/2014 |
| CN | 107841478 A | 3/2018 |
| CN | 109497281 A | 3/2019 |
| EP | 1574564 A1 | 9/2005 |
| GB | 1392813 A | 4/1975 |
| GB | 1434582 A | 5/1976 |
| JP | 3417904 B2 | 6/2003 |
| KR | 100427600 B1 | 4/2004 |
| WO | 2007083147 A2 | 7/2007 |
| WO | 2010032233 A2 | 3/2010 |
| WO | 2010033714 A1 | 3/2010 |
| WO | 2012009712 A2 | 1/2012 |
| WO | 2012101528 A2 | 8/2012 |
| WO | 2014020141 A1 | 2/2014 |
| WO | 2014067081 A1 | 5/2014 |
| WO | 2014172520 A1 | 10/2014 |
| WO | 2015057330 A1 | 4/2015 |
| WO | 2015160960 A1 | 10/2015 |
| WO | 2015175667 A1 | 11/2015 |
| WO | 2017081105 A1 | 5/2017 |
| WO | 2017151608 A1 | 9/2017 |
| WO | 2018148847 A1 | 8/2018 |
| WO | 2019090068 A1 | 5/2019 |
| WO | 2019090088 A1 | 5/2019 |
| WO | 2019141815 A1 | 7/2019 |
| WO | 2019152791 A1 | 8/2019 |
| WO | 2019/213243 A1 | 11/2019 |
| WO | 2020072578 A1 | 4/2020 |
| WO | 2021035137 A1 | 2/2021 |
| WO | 2021041603 A1 | 3/2021 |
| WO | 2023018686 A1 | 2/2023 |

OTHER PUBLICATIONS

Johnson et al. (2012). A MIQE-Compliant Real-Time PCR Assay for Aspergillus Detection., PLOSone., 7(7): 1-8.
Canning, et al., "Effect of direct-fed microbial Bacillus subtilis C-3102 on enteric health in nursery pigs after challenge with porcine epidemic diarrhea virus," Journal of Swine Health and Production, May 3, 2017, 25(3): 129-137.
Peng, et al., "Evaluation of antiviral activity of Bacillus licheniformis-fermented products against porcine epidemic diarrhea virus," AMB Express, Dec. 3, 2019, 9(191): 1-12.
Bae H.D., Yanke L.J, Cheng K.J., Selinger L.B., 1999, "A novel staining method for detecting phytase activity," Journal of Microbiological Methods, 39:1, 17-22.
Zganjer, et al. Treatment of rectal prolapse in children with cow milk injection sclerotherapy: 30-year experience, World Journal of Gastroanterology, 2008, 14(5) 740-7.

Rajendram et al. "Long-term storage and safe retrieval of DNA from microorganisms for molecular analysis using FTA matrix cards." Journal of Microbiological Methods, 2006, 67, 582-92.
Krishnani, Genbank entry KJ000877 published Feb. 2014.
Lowe, et al. "A computer program for selection of oligonucleotide primers for polymerase chain reactions." Nucleic Acids Research, 1990, 18(7) 1757-61.
McClure et al. "Assessment of DNA extracted from FTA® cards for use on the Illumina iSelect Beach Chip," BMC Research Notes, 2009, 2(107) 4 pages.
Haldar et al., "Development of a haemolysin gene-based multiplex PCR for simultaneous detection of Vibrio campbelli, Vibrio harveyi and Vibrio parahaemolyticus," Letters in Applied Microbiology, 2010, 50, 146-52.
EP Search report in EP 16789853 completed Aug. 8, 2018.
Dobbs et al. "Use of FTA Gene Guard Filter Paper for the Storage and Transportation of Tumor Cells for Molecular Testing," 2002 Arch Pathol Lab Med. vol 126, p. 56-63.
Chen et al. "Proteomic comparison of historic and recently emerged hypervirulent Clostridium difficile strains." 2013 J of Proteone Research, 12, p. 1151-1161.
International search report and written opinion for PCT/US2019/030182, mailed Aug. 8, 2019.
Choudhary et al. "Interactions of Bacillus spp. and plants—With special reference to induced systemic resistance (ISR)." Microbiologial Research 164 (2009) 493-513.
International search report and written opinion for PCT/US2020/023586, mailed May 20, 2020.
Sonune et al. "Isolation, characterization and identification of extracellular enzyme producer—Bacillus Ilcheniformis from municipal wastewater and evaluation of their biodegradability" Biotechnology Research and Innovation, Jan.-Dec. 2018, vol. 2, No. 1, pp. 37-44.
Safitri et al. "Ability of Bacterial Consortium: Bacillus coagulans, Baciluslicheniformis, Bacillus pumilus, Bacillus subtilis, Nitrosomonas sp. and Pseudomonas putida In Bioremediation of Waste Water in Cisirung Waste Water Treatment Plant" Agrolife Scientific Journal, 2015, vol. 4, No. 1, pp. 146-152.
Sumi et al., Antimicrobial peptides of the genus Bacillus: a new era for antibiotics, Nov. 19, 2014, p. 1-7.
EPA, Final Rixk assessement of Bacillus Subtilis, Feb. 1997, p. 3, 9 (1997).
European Search Report, European Application No. 20855232.3-1105 dated Aug. 31, 2023, 8 pages.
Kiarie et al. "The Role of Added Feed Enzymes in Promoting Gut Health in Swine and Poultry," Nutrition Research Reviews, Jun. 1, 2013 (Jun. 1, 2013), vol. 26, pp. 71-88. Entire document.
La Ragione et al. "Bacillus subtilis Spores Competitively Exclude *Escherichia coli* 078: K80 in Poultry," Veterinary Microbiology, Mar. 20, 2001 (Mar. 20, 2001). vol. 79, pp. 133-142. Entire document.
Harnentis et al. "Isolation, Characterization and Production of Mannanase from Thermophilic Bacteria to Increase the Feed Quality," Pakistan Journal of Nutrition 12 (4): 360-364, 2013.
PCT Search Report and Written Opinion for PCT/US2015/030578, completed Jul. 9, 2015.
Extended European Search Report, European Application No. 15792802.9-1358 dated Nov. 8, 2017, 8 pages.
Souza et al. J. Anim. Sci. vol. 90, Suppl. 3/J. Dairy Sci. Vol. 95, Suppl. 2 T281.
Credille et al. (2014). Prevalence of bacteremia in dairy cattle with acute puerperal metritis. J Vet Intern Med, 28:1606-1612.
Sheldon et al. (2009). Defining postpartum uterine disease and the mechanisms of infection and immunity in the female reproductive tract in cattle. Biol Reprod 81:1025-1032.
Abutarbush et al. (2005). Jejunal hemorrhage syndrome in dairy and beef cattle: 11 cases (2001 to 2003). Can. Vet. J. Rev. Vét. Can. 46, 711-715.
Abutarbush et al. (2004). Jejunal hemorrhage syndrome in 2 Canadian beef cows. Can. Vet. J. 45, 48-50.
Adaska et al. (2014). Jejunal hematoma in cattle: a retrospective case analysis. J. Vet. Diagn. Investig. Off. Publ. Am. Assoc. Vet. Lab. Diagn. Inc 26, 96-103.

(56) References Cited

OTHER PUBLICATIONS

Baines et al. (2011). Mouldy feed, mycotoxins and Shiga toxin—producing *Escherichia coli* colonization associated with Jejunal Hemorrhage Syndrome in beef cattle. BMC Vet. Res. 7, 24.
Ceci, L., Paradies, P., Sasanelli, M., De Caprariis, D., Guarda, F., Capucchio, M. t., and Carelli, G. (2006). Haemorrhagic Bowel Syndrome in Dairy Cattle: Possible Role of Clostridium perfringens Type A in the Disease Complex. J. Vet. Med. Ser. A 53, 518-523.
Dennison et al. (2002). Hemorrhagic bowel syndrome in dairy cattle: 22 cases (1997-2000). J. Am. Vet. Med. Assoc. 221, 686-689.
Dennison et al. (2005). Comparison of the odds of isolation, genotypes, and in vivo production of major toxins by Clostridium perfringens obtained from the gastrointestinal tract of dairy cows with hemorrhagic bowel syndrome or left-displaced abomasum. J. Am. Vet. Med. Assoc. 227, 132-138.
Malinen et al. (2003). Comparison of real-time PCR with SYBR Green I or 5'-nuclease assays and dot-blot hybridization with rDNA-targeted oligonucleotide probes in quantification of selected faecal bacteria. Microbiology. 149: 269-277.
West et al. (2007) Rapid Detection of *Escherichia coli* Virulence Factor Genes using Multiplex Real-Time TaqMan® PCR Assays. Veterinary Microbiology 122(3-4): 323-331.
Frydendahl et al. (2001). Automated 5' nuclease assay for detection of virulence factors in porcine *Escherichia coli*. Molec.Cell. Probes. 15: 151-160.
Nielsen et al. (2003). Detection and characterization of verocytotoxin-producing *Escherichia coli* by automated 5 nuclease PCR assay, Journal of ClinicalMicrobiology, vol. 41, No. 7, pp. 2884-2893.
Jinneman et al. (2003). Multiplex Real-Time PCR Method To Identify Shiga Toxin Genes stx1 and stx2 and *Escherichia coli* O157:H7/H-Serotype. Appl. Environ. Microbiol. Oct. 2003 vol. 69 No. 10 6327-6333.
Yatsuyanagi et al. (2002). Characterization of enteropathogenic and enteroaggregative *Escherichia coli* isolated from diarrheal outbreaks, Journal of Clinical Microbiology, vol. 40, No. 1, pp. 294-297.
Albini et al. (2010). Real-time multiplex PCR assays for reliable detection of Clostridium perfringens toxin genes in animal isolates, Veterinary Microbiology, 127 (1-2): 179-185.
Miller et al., "Sanitary Landfill Simulation: Test Parameters and a Simulator Conceptual Design," Naval Facilities Engineering Command: Civil Engineering Laboratory, Oct. 20, 1976 (Oct. 20, 1976), pp. 1-47. Retrieved from the Internet: <https://apps.dtic.mil/dtic/tr/fulltext/u2/a030998.pdf>.
Fei et al., "A laboratory landfill simulator for physical, geotechnical, chemical and microbial characterization of solid waste biodegradation processes," Couples Phenomena in Environmental Geotechnics, May 20, 2013 (May 30, 2013), Taylor & Francis Group, London, pp. 321-327.
Mahar et al., "Modeling and simulation of landfill gas production from pretreated MSW landfill simulator," Frontiers of Environmental Science & Engineering, Apr. 15, 2014 (Apr. 15, 2014), vol. 10, Iss. 1, pp. 159-167.
Karigar et al., "Role of Microbial Enzymes in the Bioremediation of Pollutants: A Review," Enzyme Research, vol. 2011, Article ID 805187, 11 pages.
Schmidt et al., "New Concepts of microbial treatment processes for the nitrogen removal in wastewater," 2003.
Ramachandran et al., "A Broad-Spectrum Antimicrobial Activity of Bacillus subtilis RLID 12.1 ," 2014.
Supp. European Search Report, European Application No. 20858946, dated Aug. 23, 2023.
Sonune et al., "Isolation, characterization and identification of extracellular enzyme producer Bacillus licheniformis from municipal wastewater and evaluation of their biodegradability." Biotechnology Research and Innovation, vol. 2, No. 1, Jan. 1, 2018, pp. 37-44.
Cohn et al., "Bacillus Strains Improving Health and Performance of Production Animals." IP.com, ip.com Inc., Feb. 11, 2016, p. 36, line 54.

\* cited by examiner

DIRECT-FED MICROBIALS

CROSS-REFERENCE TO RELATED APPLICATIONS

This application is a Divisional Application of U.S. application Ser. No. 16/454,593, filed Jun. 27, 2019, which is a Continuation Application of U.S. application Ser. No. 15/445,193, filed Feb. 28, 2017, and issued as U.S. Pat. No. 10,335,440, which claims priority under 35 U.S.C. § 119(e) to U.S. Provisional Application Ser. No. 62/301,438 filed Feb. 29, 2016, and U.S. Provisional Application Ser. No. 62/364,271 filed Jul. 19, 2016, the disclosures of which are hereby expressly incorporated by reference in their entirety.

FIELD OF THE DISCLOSURE

The invention relates to direct-fed microbials for use in *E. coli* inhibition in animals. More particularly, the invention relates to isolated *Bacillus* strains 101, 235, 77, 177, and 102, and strains having all of the identifying characteristics of these strains, for a use comprising the above-mentioned use. The invention can also be used for treatment of plants and in food processing.

BACKGROUND AND SUMMARY OF THE INVENTION

The present invention relates to direct-fed microbial (DFM) compositions and methods for *E. coli* inhibition in an animal. An animal's gastrointestinal tract is constantly challenged by large numbers of bacteria, viruses, and protozoa found in feed, bedding, and the environment. The gastrointestinal tract has a sophisticated system to counter these potential pathogens consisting of physical, chemical, and immunological lines of defense. Beneficial bacteria are an important part of this system because they provide animals with bacteria that assist in establishment (or reestablishment) of a normal bacterial profile, they strengthen the animal's immune system, and they help to fight disease (e.g., disease caused by *E. coli* in animals). Due to the importance of preventing and treating *E. coli* disease in animals, both to the agricultural industry, and to the human food supply, direct-fed microbial strains are needed that inhibit *E. coli* in animals, such as agricultural animals.

Applicants have developed direct-fed microbials that result in *E. coli* inhibition in animals. The direct-fed microbials and compositions comprising the direct-fed microbials described herein offer a commercial benefit by providing *E. coli* inhibition in animals, such as agricultural animals. In addition, the direct-fed microbial compositions described herein result in a reduction or elimination in the use of antibiotics which reduces the overall cost of animal feed.

Methods and compositions are provided for inhibiting *E. coli* in animals. In various embodiments, the animal can be selected from the group consisting of a poultry species, a porcine species, a bovine species, an ovine species, an equine species, and a companion animal. In the embodiment where the animal is a poultry species, the poultry species can be a broiler chicken. In the embodiment where the animal is a porcine species, the porcine species can be selected from the group consisting of a grow finish pig, a nursery pig, a sow, and a breeding stock pig.

In various embodiments, the compositions for use in the methods described herein can be a commercial package, a feed additive for an animal feed composition, an additive for the drinking water of an animal, or an animal feed composition (e.g., a complete feed), each comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

In one embodiment of the methods described herein, a method is provided of feeding an animal. The method comprises the step of administering to the animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain causes *E. coli* inhibition in the animal.

In another embodiment of the methods described herein, a method is provided of controlling a detrimental effect of *E. coli*. The method comprises the steps of administering to an animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, and controlling the detrimental effect of *E. coli* in the animal.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the EXAMPLES are applicable to any of the following embodiments of the invention described in the numbered clauses below.

1. A method of feeding an animal, the method comprising the step of administering to the animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain causes *E. coli* inhibition in the animal.

2. The method of clause 1 wherein the animal is selected from the group consisting of a poultry species, a porcine species, a bovine species, an ovine species, an equine species, and a companion animal.

3. The method of clause 2 wherein the poultry species is a broiler chicken.

4. The method of any one of clauses 1 to 3 wherein the *E. coli* inhibition prevents *E. coli* disease in the animal.

5. The method of any one of clauses 1 to 3 wherein the *E. coli* inhibition reduces *E. coli* disease in the animal.

6. The method of clause 2 wherein the animal is a porcine species and the porcine species is selected from the group consisting of a grow finish pig, a nursery pig, a sow, and a breeding stock pig.

7. The method of any one of clauses 1 to 6 wherein the *Bacillus* strain produces an enzyme selected from the group consisting of an α-galactosidase, a protease, a lipase, an amylase, a xylanase, a cellulase, and combinations thereof.

8. The method of any one of clauses 1 to 7 further comprising the step of administering to the animal another bacterial strain selected from the group consisting of another *Bacillus* strain, a lactic acid bacterial strain, and combinations thereof.

9. The method of any one of clauses 1 to 8 wherein the strain administered is *Bacillus* strain 101 (NRRL No. B-67218) or a strain having all of the identifying characteristics of *Bacillus* strain 101 (NRRL No. B-67218).

10. The method of any one of clauses 1 to 8 wherein the strain administered is *Bacillus* strain 235 (NRRL No. B-67219) or a strain having all of the identifying characteristics of *Bacillus* strain 235 (NRRL No. B-67219).

11. The method of any one of clauses 1 to 8 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in a single composition.

12. The method of any one of clauses 1 to 8 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in separate compositions.

13. The method of any one of clauses 1 to 12 wherein the *Bacillus* strain is administered in the feed composition at a dose of about $1.0 \times 10^3$ CFU/gram of the feed composition to about $5.0 \times 10^{12}$ CFU/gram of the feed composition.

14. The method of any one of clauses 1 to 12 wherein the *Bacillus* strain is administered in the feed composition at a dose of about $1.0 \times 10^3$ CFU/gram of the feed composition to about $1.0 \times 10^7$ CFU/gram of the feed composition.

15. The method of any one of clauses 1 to 14 wherein the *Bacillus* strain is administered in the feed composition at a dose greater than about $7.0 \times 10^4$ CFU/gram of the feed composition.

16. The method of any one of clauses 1 to 15 wherein the *Bacillus* strain is administered in the feed composition at a dose of about $7.3 \times 10^4$ CFU/gram of the feed composition.

17. The method of any one of clauses 1 to 16 wherein the *Bacillus* strain is isolated from a high performing grow finish pig.

18. The method of any one of clauses 1 to 17 further comprising the step of administering an antibiotic to the animal.

19. The method of any one of clauses 1 to 18 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

20. The method of clause 19 wherein the enzyme is an NSPase or a phytase.

21. The method of any one of clauses 1 to 20 wherein the microbial balance in the animal is maintained.

22. The method of clause 2 wherein the animal is a companion animal.

23. The method of clause 22 wherein the animal is a canine species or a feline species.

24. The method of clause 2 wherein the animal is a sow and the *Bacillus* strain is administered during lactation.

25. The method of clause 2 wherein the animal is a sow and the *Bacillus* strain is administered during gestation.

26. The method of any one of clauses 1 to 25 wherein the feed composition is administered daily to the animal.

27. The method of clause 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

28. A method of controlling a detrimental effect of *E. coli*, the method comprising the steps of administering to an animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, and controlling the detrimental effect of *E. coli* in the animal.

29. The method of clause 28 wherein the animal is selected from the group consisting of a poultry species, a porcine species, a bovine species, an ovine species, an equine species, and a companion animal.

30. The method of clause 29 wherein the poultry species is a broiler chicken.

31. The method of any one of clauses 28 to 30 wherein controlling the detrimental effect of *E. coli* comprises inhibiting *E. coli* disease in the animal.

32. The method of any one of clauses 28 to 30 wherein controlling the detrimental effect of *E. coli* comprises reducing *E. coli* disease in the animal.

33. The method of clause 29 wherein the animal is a porcine species and the porcine species is selected from the group consisting of a grow finish pig, a nursery pig, a sow, and a breeding stock pig.

34. The method of any one of clauses 28 to 33 wherein the *Bacillus* strain produces an enzyme selected from the group consisting of an α-galactosidase, a protease, a lipase, an amylase, a xylanase, a cellulase, and combinations thereof.

35. The method of any one of clauses 28 to 34 further comprising the step of administering to the animal another bacterial strain selected from the group consisting of another *Bacillus* strain, a lactic acid bacterial strain, and combinations thereof.

36. The method of any one of clauses 28 to 35 wherein the strain administered is *Bacillus* strain 101 (NRRL No. B-67218) or a strain having all of the identifying characteristics of *Bacillus* strain 101 (NRRL No. B-67218).

37. The method of any one of clauses 28 to 35 wherein the strain administered is *Bacillus* strain 235 (NRRL No. B-67219) or a strain having all of the identifying characteristics of *Bacillus* strain 235 (NRRL No. B-67219).

38. The method of any one of clauses 28 to 35 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in a single composition.

39. The method of any one of clauses 28 to 35 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in separate compositions.

40. The method of any one of clauses 28 to 39 wherein the *Bacillus* strain is administered in the feed composition at a dose of about $1.0 \times 10^3$ CFU/gram of the feed composition to about $5.0 \times 10^{12}$ CFU/gram of the feed composition.

41. The method of any one of clauses 28 to 40 wherein the *Bacillus* strain is administered in the feed composition at a dose of about $1.0 \times 10^3$ CFU/gram of the feed composition to about $1.0 \times 10^7$ CFU/gram of the feed composition.

42. The method of any one of clauses 28 to 41 wherein the *Bacillus* strain is administered in the feed composition at a dose greater than about $7.0 \times 10^4$ CFU/gram of the feed composition.

43. The method of any one of clauses 28 to 42 wherein the *Bacillus* strain is administered in the feed composition at a dose of about $7.3 \times 10^4$ CFU/gram of the feed composition.

44. The method of any one of clauses 28 to 43 wherein the *Bacillus* strain is isolated from a high performing grow finish pig.

45. The method of any one of clauses 28 to 44 further comprising the step of administering an antibiotic to the animal.

46. The method of any one of clauses 28 to 45 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

47. The method of clause 46 wherein the enzyme is an NSPase or a phytase.

48. The method of any one of clauses 28 to 47 wherein controlling the detrimental effect of *E. coli* comprises maintaining the microbial balance in the animal.

49. The method of clause 29 wherein the animal is a companion animal.

50. The method of clause 49 wherein the animal is a canine species or a feline species.

51. The method of clause 29 wherein the animal is a sow and the *Bacillus* strain is administered during lactation.

52. The method of clause 29 wherein the animal is a sow and the *Bacillus* strain is administered during gestation.

53. The method of any one of clauses 28 to 52 wherein the feed composition is administered daily to the animal.

54. The method of clause 28 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

55. A commercial package comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

56. A feed additive for an animal feed comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

57. An additive for the drinking water of an animal comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

58. An animal feed composition comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

59. The commercial package, feed additive, feed composition, or additive for the drinking water of the animal of any one of clauses 55 to 58 wherein the *Bacillus* strain causes an effect selected from the group consisting of preventing *E. coli* disease, reducing *E. coli* disease, maintaining the microbial balance of the animal, and combinations thereof.

60. The commercial package, feed additive, feed composition, or additive for the drinking water of the animal of any one of clauses 55 to 59, wherein the *Bacillus* strain reduces *E. coli* disease in the animal.

61. The feed additive or additive for the drinking water of the animal of clause 56 or 57 in the form of a concentrate.

62. The feed additive or additive for the drinking water of the animal of clause 56 or 57 in the form of a super concentrate.

63. The feed additive, feed composition, or additive for the drinking water of the animal of any one of clauses 56 to 62 in dry form.

64. The feed composition of clause 63 in pelleted form.

65. The commercial package of clause 55 wherein the strains are in a form selected from the group consisting of a powder, a liquid, and a pellet form.

66. The commercial package, feed additive, additive for the drinking water of the animal, or feed composition of any one of clauses 55 to 65 further comprising a carrier for the *Bacillus* strains.

67. The commercial package, feed additive, additive for the drinking water of the animal, or feed composition of clause 66 wherein the carrier is selected from the group consisting of a bran, rice hulls, a salt, a dextrin, and combinations thereof.

68. The commercial package, feed additive, additive for the drinking water of the animal, or feed composition of any one of clauses 55 to 67 in a bag.

69. The commercial package, feed additive, additive for the drinking water of the animal, or feed composition of clause 68 wherein the bag is a plastic bag.

70. The commercial package, feed additive, additive for the drinking water of the animal, or feed composition of any one of clauses 55 to 69 further comprising instructions for use of one or more of the *Bacillus* strains.

71. The commercial package, feed additive, feed composition, or additive for the drinking water of the animal of any one of clauses 68 to 70 in a 20-pound bag.

72. The commercial package, feed additive, feed composition, or additive for the drinking water of the animal of any one of clauses 68 to 70 in a 50-pound bag.

73. The feed additive or additive for the drinking water of the animal of any one of clauses 56, 57, 59 to 63, or 66 to 72 in powder form.

74. The feed additive or additive for the drinking water of the animal of any one of clauses 56, 57, 59 to 60, or 68 to 70 in liquid form.

75. The commercial package, feed additive, additive for the drinking water of the animal, or feed composition of any one of clauses 55 to 74 in a container for commercial use.

76. The commercial package, feed additive, additive for the drinking water of the animal, or feed composition of clause 75 wherein the container comprises plastic.

77. The commercial package, feed additive, additive for the drinking water of the animal, or feed composition of clause 75 wherein the container comprises paper.

78. The commercial package, feed additive, additive for the drinking water of the animal, or feed composition of any one of clauses 55 to 77 further comprising a binder.

79. The commercial package, feed additive, additive for the drinking water of the animal, or feed composition of clause 78 wherein the binder is selected from the group consisting of clay, yeast cell wall components, aluminum silicate, and glucan, or combinations thereof.

80. A method of feeding an animal, the method comprising the step of administering to the animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

81. The method of clause 80 wherein the animal is selected from the group consisting of a poultry species, a porcine species, a bovine species, an ovine species, an equine species, and a companion animal.

82. The method of clause 81 wherein the poultry species is a broiler chicken.

83. The method of any one of clauses 80 to 82 wherein the strain causes *E. coli* inhibition which prevents *E. coli* disease in the animal.

84. The method of any one of clauses 80 to 82 wherein the strain causes *E. coli* inhibition which reduces *E. coli* disease in the animal.

85. The method of clause 81 wherein the animal is a porcine species and the porcine species is selected from the group consisting of a grow finish pig, a nursery pig, a sow, and a breeding stock pig.

86. The method of any one of clauses 80 to 85 wherein the *Bacillus* strain produces an enzyme selected from the group consisting of an α-galactosidase, a protease, a lipase, an amylase, a xylanase, a cellulase, and combinations thereof.

87. The method of any one of clauses 80 to 86 further comprising the step of administering to the animal another bacterial strain selected from the group consisting of another *Bacillus* strain, a lactic acid bacterial strain, and combinations thereof.

88. The method of any one of clauses 80 to 87 wherein the strain administered is *Bacillus* strain 101 (NRRL No. B-67218) or a strain having all of the identifying characteristics of *Bacillus* strain 101 (NRRL No. B-67218).

89. The method of any one of clauses 80 to 87 wherein the strain administered is *Bacillus* strain 235 (NRRL No. B-67219) or a strain having all of the identifying characteristics of *Bacillus* strain 235 (NRRL No. B-67219).

90. The method of any one of clauses 80 to 87 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in a single composition.

91. The method of any one of clauses 80 to 87 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in separate compositions.

92. The method of any one of clauses 80 to 91 wherein the *Bacillus* strain is administered in the feed composition at a dose of about $1.0 \times 10^3$ CFU/gram of the feed composition to about $5.0 \times 10^{12}$ CFU/gram of the feed composition.

93. The method of any one of clauses 80 to 92 wherein the *Bacillus* strain is administered in the feed composition at a dose of about $1.0 \times 10^3$ CFU/gram of the feed composition to about $1.0 \times 10^7$ CFU/gram of the feed composition.

94. The method of any one of clauses 80 to 93 wherein the *Bacillus* strain is administered in the feed composition at a dose greater than about $7.0 \times 10^4$ CFU/gram of the feed composition.

95. The method of any one of clauses 80 to 94 wherein the *Bacillus* strain is administered in the feed composition at a dose of about $7.3 \times 10^4$ CFU/gram of the feed composition.

96. The method of any one of clauses 80 to 95 wherein the *Bacillus* strain is isolated from a high performing grow finish pig.

97. The method of any one of clauses 80 to 96 further comprising the step of administering an antibiotic to the animal.

98. The method of any one of clauses 80 to 97 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

99. The method of clause 98 wherein the enzyme is an NSPase or a phytase.

100. The method of any one of clauses 80 to 99 wherein the microbial balance in the animal is maintained.

101. The method of clause 81 wherein the animal is a companion animal.

102. The method of clause 101 wherein the animal is a canine species or a feline species.

103. The method of clause 81 wherein the animal is a sow and the *Bacillus* strain is administered during lactation.

104. The method of clause 81 wherein the animal is a sow and the *Bacillus* strain is administered during gestation.

105. The method of any one of clauses 80 to 104 wherein the feed composition is administered daily to the animal.

106. The method of clause 80 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

107. The method of any one of clauses 1 to 8, 28 to 35, or 80 to 87 wherein the strain administered is *Bacillus* strain 77 (NRRL No. B-67274) or a strain having all of the identifying characteristics of *Bacillus* strain 77 (NRRL No. B-67274).

108. The method of any one of clauses 1 to 8, 28 to 35, or 80 to 87 wherein the strain administered is *Bacillus* strain 177 (NRRL No. B-67275) or a strain having all of the identifying characteristics of *Bacillus* strain 177 (NRRL No. B-67275).

109. The method of any one of clauses 1 to 8, 28 to 35, or 80 to 87 wherein the strain administered is *Bacillus* strain 102 (NRRL No. B-67276), or a strain having all of the identifying characteristics of *Bacillus* strain 102 (NRRL No. B-67276).

110. The method of any one of clauses 1 to 8, 28 to 35, or 80 to 87 wherein isolated *Bacillus* strains comprising *Bacillus* strains 101 (NRRL No. B-67218), 235 (NRRL No. B-67219), 77 (NRRL No. B-67274), 177 (NRRL No. B-67275), and 102 (NRRL No. B-67276) are administered in combination in separate compositions.

111. The method of any one of clauses 1 to 8, 28 to 35, or 80 to 87 wherein isolated *Bacillus* strains comprising *Bacillus* strains 101 (NRRL No. B-67218), 235 (NRRL No. B-67219), 77 (NRRL No. B-67274), 177 (NRRL No. B-67275), and 102 (NRRL No. B-67276) are administered in combination in a single composition.

112. The method of any one of clauses 1 to 8, 28 to 35, or 80 to 87 wherein isolated *Bacillus* strains comprising *Bacillus* strains 101 (NRRL No. B-67218), 235 (NRRL No. B-67219), 177 (NRRL No. B-67275), and 102 (NRRL No. B-67276) are administered in combination in separate compositions.

113. The method of any one of clauses 1 to 8, 28 to 35, or 80 to 87 wherein isolated *Bacillus* strains comprising *Bacillus* strains 101 (NRRL No. B-67218), 235 (NRRL No. B-67219), 177 (NRRL No. B-67275), and 102 (NRRL No. B-67276) are administered in combination in a single composition.

DETAILED DESCRIPTION OF ILLUSTRATIVE EMBODIMENTS

Methods and compositions are provided for inhibiting *E. coli* in animals, such as agricultural animals. In various embodiments, the compositions for use in the methods described herein can be a commercial package, a feed additive for an animal feed composition, an additive for the drinking water of an animal, or an animal feed composition (e.g., a complete feed), each comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

In one embodiment of the methods described herein, a method is provided of feeding an animal. The method comprises the step of administering to the animal a feed composition or drinking water comprising an effective amount of an additive comprising an isolated *Bacillus* strain selected from the group consisting of *Bacillus* strain 101

(NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain causes *E. coli* inhibition in the animal.

In another embodiment of the methods described herein, a method is provided of controlling a detrimental effect of *E. coli*. The method comprises the steps of administering to an animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, and controlling the detrimental effect of *E. coli* in the animal.

The following clauses, and combinations thereof, provide various additional illustrative aspects of the invention described herein. The various embodiments described in this section titled "DETAILED DESCRIPTION OF ILLUSTRATIVE EMBODIMENTS" are applicable to any of the following embodiments of the invention described in the numbered clauses below.

1. A method of feeding an animal, the method comprising the step of administering to the animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain causes *E. coli* inhibition in the animal.

2. The method of clause 1 wherein the animal is selected from the group consisting of a poultry species, a porcine species, a bovine species, an ovine species, an equine species, and a companion animal.

3. The method of clause 2 wherein the poultry species is a broiler chicken.

4. The method of any one of clauses 1 to 3 wherein the *E. coli* inhibition prevents *E. coli* disease in the animal.

5. The method of any one of clauses 1 to 3 wherein the *E. coli* inhibition reduces *E. coli* disease in the animal.

6. The method of clause 2 wherein the animal is a porcine species and the porcine species is selected from the group consisting of a grow finish pig, a nursery pig, a sow, and a breeding stock pig.

7. The method of any one of clauses 1 to 6 wherein the *Bacillus* strain produces an enzyme selected from the group consisting of an α-galactosidase, a protease, a lipase, an amylase, a xylanase, a cellulase, and combinations thereof.

8. The method of any one of clauses 1 to 7 further comprising the step of administering to the animal another bacterial strain selected from the group consisting of another *Bacillus* strain, a lactic acid bacterial strain, and combinations thereof.

9. The method of any one of clauses 1 to 8 wherein the strain administered is *Bacillus* strain 101 (NRRL No. B-67218) or a strain having all of the identifying characteristics of *Bacillus* strain 101 (NRRL No. B-67218).

10. The method of any one of clauses 1 to 8 wherein the strain administered is *Bacillus* strain 235 (NRRL No. B-67219) or a strain having all of the identifying characteristics of *Bacillus* strain 235 (NRRL No. B-67219).

11. The method of any one of clauses 1 to 8 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in a single composition.

12. The method of any one of clauses 1 to 8 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in separate compositions.

13. The method of any one of clauses 1 to 12 wherein the *Bacillus* strain is administered in the feed composition at a dose of about $1.0 \times 10^3$ CFU/gram of the feed composition to about $5.0 \times 10^{12}$ CFU/gram of the feed composition.

14. The method of any one of clauses 1 to 12 wherein the *Bacillus* strain is administered in the feed composition at a dose of about $1.0 \times 10^3$ CFU/gram of the feed composition to about $1.0 \times 10^7$ CFU/gram of the feed composition.

15. The method of any one of clauses 1 to 14 wherein the *Bacillus* strain is administered in the feed composition at a dose greater than about $7.0 \times 10^4$ CFU/gram of the feed composition.

16. The method of any one of clauses 1 to 15 wherein the *Bacillus* strain is administered in the feed composition at a dose of about $7.3 \times 10^4$ CFU/gram of the feed composition.

17. The method of any one of clauses 1 to 16 wherein the *Bacillus* strain is isolated from a high performing grow finish pig.

18. The method of any one of clauses 1 to 17 further comprising the step of administering an antibiotic to the animal.

19. The method of any one of clauses 1 to 18 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

20. The method of clause 19 wherein the enzyme is an NSPase or a phytase.

21. The method of any one of clauses 1 to 20 wherein the microbial balance in the animal is maintained.

22. The method of clause 2 wherein the animal is a companion animal.

23. The method of clause 22 wherein the animal is a canine species or a feline species.

24. The method of clause 2 wherein the animal is a sow and the *Bacillus* strain is administered during lactation.

25. The method of clause 2 wherein the animal is a sow and the *Bacillus* strain is administered during gestation.

26. The method of any one of clauses 1 to 25 wherein the feed composition is administered daily to the animal.

27. The method of clause 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

28. A method of controlling a detrimental effect of *E. coli*, the method comprising the steps of administering to an animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, and controlling the detrimental effect of *E. coli* in the animal.

29. The method of clause 28 wherein the animal is selected from the group consisting of a poultry species, a porcine species, a bovine species, an ovine species, an equine species, and a companion animal.

30. The method of clause 29 wherein the poultry species is a broiler chicken.

31. The method of any one of clauses 28 to 30 wherein controlling the detrimental effect of *E. coli* comprises inhibiting *E. coli* disease in the animal.

32. The method of any one of clauses 28 to 30 wherein controlling the detrimental effect of *E. coli* comprises reducing *E. coli* disease in the animal.

33. The method of clause 29 wherein the animal is a porcine species and the porcine species is selected from the group consisting of a grow finish pig, a nursery pig, a sow, and a breeding stock pig.

34. The method of any one of clauses 28 to 33 wherein the *Bacillus* strain produces an enzyme selected from the group consisting of an α-galactosidase, a protease, a lipase, an amylase, a xylanase, a cellulase, and combinations thereof.

35. The method of any one of clauses 28 to 34 further comprising the step of administering to the animal another bacterial strain selected from the group consisting of another *Bacillus* strain, a lactic acid bacterial strain, and combinations thereof.

36. The method of any one of clauses 28 to 35 wherein the strain administered is *Bacillus* strain 101 (NRRL No. B-67218) or a strain having all of the identifying characteristics of *Bacillus* strain 101 (NRRL No. B-67218).

37. The method of any one of clauses 28 to 35 wherein the strain administered is *Bacillus* strain 235 (NRRL No. B-67219) or a strain having all of the identifying characteristics of *Bacillus* strain 235 (NRRL No. B-67219).

38. The method of any one of clauses 28 to 35 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in a single composition.

39. The method of any one of clauses 28 to 35 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in separate compositions.

40. The method of any one of clauses 28 to 39 wherein the *Bacillus* strain is administered in the feed composition at a dose of about $1.0 \times 10^3$ CFU/gram of the feed composition to about $5.0 \times 10^{12}$ CFU/gram of the feed composition.

41. The method of any one of clauses 28 to 40 wherein the *Bacillus* strain is administered in the feed composition at a dose of about $1.0 \times 10^3$ CFU/gram of the feed composition to about $1.0 \times 10^7$ CFU/gram of the feed composition.

42. The method of any one of clauses 28 to 41 wherein the *Bacillus* strain is administered in the feed composition at a dose greater than about $7.0 \times 10^4$ CFU/gram of the feed composition.

43. The method of any one of clauses 28 to 42 wherein the *Bacillus* strain is administered in the feed composition at a dose of about $7.3 \times 10^4$ CFU/gram of the feed composition.

44. The method of any one of clauses 28 to 43 wherein the *Bacillus* strain is isolated from a high performing grow finish pig.

45. The method of any one of clauses 28 to 44 further comprising the step of administering an antibiotic to the animal.

46. The method of any one of clauses 28 to 45 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

47. The method of clause 46 wherein the enzyme is an NSPase or a phytase.

48. The method of any one of clauses 28 to 47 wherein controlling the detrimental effect of *E. coli* comprises maintaining the microbial balance in the animal.

49. The method of clause 29 wherein the animal is a companion animal.

50. The method of clause 49 wherein the animal is a canine species or a feline species.

51. The method of clause 29 wherein the animal is a sow and the *Bacillus* strain is administered during lactation.

52. The method of clause 29 wherein the animal is a sow and the *Bacillus* strain is administered during gestation.

53. The method of any one of clauses 28 to 52 wherein the feed composition is administered daily to the animal.

54. The method of clause 28 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

55. A commercial package comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

56. A feed additive for an animal feed comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

57. An additive for the drinking water of an animal comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

58. An animal feed composition comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

59. The commercial package, feed additive, feed composition, or additive for the drinking water of the animal of any one of clauses 55 to 58 wherein the *Bacillus* strain causes an effect selected from the group consisting of preventing *E. coli* disease, reducing *E. coli* disease, maintaining the microbial balance of the animal, and combinations thereof.

60. The commercial package, feed additive, feed composition, or additive for the drinking water of the animal of any one of clauses 55 to 59, wherein the *Bacillus* strain reduces *E. coli* disease in the animal.

61. The feed additive or additive for the drinking water of the animal of clause 56 or 57 in the form of a concentrate.

62. The feed additive or additive for the drinking water of the animal of clause 56 or 57 in the form of a super concentrate.

63. The feed additive, feed composition, or additive for the drinking water of the animal of any one of clauses 56 to 62 in dry form.

64. The feed composition of clause 63 in pelleted form.

65. The commercial package of clause 55 wherein the strains are in a form selected from the group consisting of a powder, a liquid, and a pellet form.

66. The commercial package, feed additive, additive for the drinking water of the animal, or feed composition of any one of clauses 55 to 65 further comprising a carrier for the *Bacillus* strains.

67. The commercial package, feed additive, additive for the drinking water of the animal, or feed composition of clause 66 wherein the carrier is selected from the group consisting of a bran, rice hulls, a salt, a dextrin, and combinations thereof.

68. The commercial package, feed additive, additive for the drinking water of the animal, or feed composition of any one of clauses 55 to 67 in a bag.

69. The commercial package, feed additive, additive for the drinking water of the animal, or feed composition of clause 68 wherein the bag is a plastic bag.

70. The commercial package, feed additive, additive for the drinking water of the animal, or feed composition of any one of clauses 55 to 69 further comprising instructions for use of one or more of the *Bacillus* strains.

71. The commercial package, feed additive, feed composition, or additive for the drinking water of the animal of any one of clauses 68 to 70 in a 20-pound bag.

72. The commercial package, feed additive, feed composition, or additive for the drinking water of the animal of any one of clauses 68 to 70 in a 50-pound bag.

73. The feed additive or additive for the drinking water of the animal of any one of clauses 56, 57, 59 to 63, or 66 to 72 in powder form.

74. The feed additive or additive for the drinking water of the animal of any one of clauses 56, 57, 59 to 60, or 68 to 70 in liquid form.

75. The commercial package, feed additive, additive for the drinking water of the animal, or feed composition of any one of clauses 55 to 74 in a container for commercial use.

76. The commercial package, feed additive, additive for the drinking water of the animal, or feed composition of clause 75 wherein the container comprises plastic.

77. The commercial package, feed additive, additive for the drinking water of the animal, or feed composition of clause 75 wherein the container comprises paper.

78. The commercial package, feed additive, additive for the drinking water of the animal, or feed composition of any one of clauses 55 to 77 further comprising a binder.

79. The commercial package, feed additive, additive for the drinking water of the animal, or feed composition of clause 78 wherein the binder is selected from the group consisting of clay, yeast cell wall components, aluminum silicate, and glucan, or combinations thereof.

80. A method of feeding an animal, the method comprising the step of administering to the animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

81. The method of clause 80 wherein the animal is selected from the group consisting of a poultry species, a porcine species, a bovine species, an ovine species, an equine species, and a companion animal.

82. The method of clause 81 wherein the poultry species is a broiler chicken.

83. The method of any one of clauses 80 to 82 wherein the strain causes *E. coli* inhibition which prevents *E. coli* disease in the animal.

84. The method of any one of clauses 80 to 82 wherein the strain causes *E. coli* inhibition which reduces *E. coli* disease in the animal.

85. The method of clause 81 wherein the animal is a porcine species and the porcine species is selected from the group consisting of a grow finish pig, a nursery pig, a sow, and a breeding stock pig.

86. The method of any one of clauses 80 to 85 wherein the *Bacillus* strain produces an enzyme selected from the group consisting of an α-galactosidase, a protease, a lipase, an amylase, a xylanase, a cellulase, and combinations thereof.

87. The method of any one of clauses 80 to 86 further comprising the step of administering to the animal another bacterial strain selected from the group consisting of another *Bacillus* strain, a lactic acid bacterial strain, and combinations thereof.

88. The method of any one of clauses 80 to 87 wherein the strain administered is *Bacillus* strain 101 (NRRL No. B-67218) or a strain having all of the identifying characteristics of *Bacillus* strain 101 (NRRL No. B-67218).

89. The method of any one of clauses 80 to 87 wherein the strain administered is *Bacillus* strain 235 (NRRL No. B-67219) or a strain having all of the identifying characteristics of *Bacillus* strain 235 (NRRL No. B-67219).

90. The method of any one of clauses 80 to 87 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in a single composition.

91. The method of any one of clauses 80 to 87 wherein *Bacillus* strain 101 (NRRL No. B-67218), or a strain having all of the identifying characteristics of *Bacillus* strain 101 (NRRL No. B-67218), and *Bacillus* strain 235 (NRRL No. B-67219), or a strain having all of the identifying characteristics of *Bacillus* strain 235 (NRRL No. B-67219), are administered in combination in separate compositions.

92. The method of any one of clauses 80 to 91 wherein the *Bacillus* strain is administered in the feed composition at a dose of about $1.0 \times 10^3$ CFU/gram of the feed composition to about $5.0 \times 10^{12}$ CFU/gram of the feed composition.

93. The method of any one of clauses 80 to 92 wherein the *Bacillus* strain is administered in the feed composition at a dose of about $1.0 \times 10^3$ CFU/gram of the feed composition to about $1.0 \times 10^7$ CFU/gram of the feed composition.

94. The method of any one of clauses 80 to 93 wherein the *Bacillus* strain is administered in the feed composition at a dose greater than about $7.0 \times 10^4$ CFU/gram of the feed composition.

95. The method of any one of clauses 80 to 94 wherein the *Bacillus* strain is administered in the feed composition at a dose of about $7.3 \times 10^4$ CFU/gram of the feed composition.

96. The method of any one of clauses 80 to 95 wherein the *Bacillus* strain is isolated from a high performing grow finish pig.

97. The method of any one of clauses 80 to 96 further comprising the step of administering an antibiotic to the animal.

98. The method of any one of clauses 80 to 97 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

99. The method of clause 98 wherein the enzyme is an NSPase or a phytase.

100. The method of any one of clauses 80 to 99 wherein the microbial balance in the animal is maintained.

101. The method of clause 81 wherein the animal is a companion animal.

102. The method of clause 101 wherein the animal is a canine species or a feline species.

103. The method of clause 81 wherein the animal is a sow and the *Bacillus* strain is administered during lactation.

104. The method of clause 81 wherein the animal is a sow and the *Bacillus* strain is administered during gestation.

105. The method of any one of clauses 80 to 104 wherein the feed composition is administered daily to the animal.

106. The method of clause 80 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

107. The method of any one of clauses 1 to 8, 28 to 35, or 80 to 87 wherein the strain administered is *Bacillus* strain 77 (NRRL No. B-67274) or a strain having all of the identifying characteristics of *Bacillus* strain 77 (NRRL No. B-67274).

108. The method of any one of clauses 1 to 8, 28 to 35, or 80 to 87 wherein the strain administered is *Bacillus* strain 177 (NRRL No. B-67275) or a strain having all of the identifying characteristics of *Bacillus* strain 177 (NRRL No. B-67275).

109. The method of any one of clauses 1 to 8, 28 to 35, or 80 to 87 wherein the strain administered is *Bacillus* strain 102 (NRRL No. B-67276), or a strain having all of the identifying characteristics of *Bacillus* strain 102 (NRRL No. B-67276).

110. The method of any one of clauses 1 to 8, 28 to 35, or 80 to 87 wherein isolated *Bacillus* strains comprising *Bacillus* strains 101 (NRRL No. B-67218), 235 (NRRL No. B-67219), 77 (NRRL No. B-67274), 177 (NRRL No. B-67275), and 102 (NRRL No. B-67276) are administered in combination in separate compositions.

111. The method of any one of clauses 1 to 8, 28 to 35, or 80 to 87 wherein isolated *Bacillus* strains comprising *Bacillus* strains 101 (NRRL No. B-67218), 235 (NRRL No. B-67219), 77 (NRRL No. B-67274), 177 (NRRL No. B-67275), and 102 (NRRL No. B-67276) are administered in combination in a single composition.

112. The method of any one of clauses 1 to 8, 28 to 35, or 80 to 87 wherein isolated *Bacillus* strains comprising *Bacillus* strains 101 (NRRL No. B-67218), 235 (NRRL No. B-67219), 177 (NRRL No. B-67275), and 102 (NRRL No. B-67276) are administered in combination in separate compositions.

113. The method of any one of clauses 1 to 8, 28 to 35, or 80 to 87 wherein isolated *Bacillus* strains comprising *Bacillus* strains 101 (NRRL No. B-67218), 235 (NRRL No. B-67219), 177 (NRRL No. B-67275), and 102 (NRRL No. B-67276) are administered in combination in a single composition.

In various embodiments, the animal to which a feed additive, a feed composition, or drinking water as described herein is administered can be selected from the group consisting of a poultry species, a porcine species, a bovine species, an ovine species, an equine species, and a companion animal. In the embodiment where the animal is a companion animal, the companion animal can be, for example, a canine species or a feline species. In the embodiment where the animal is a porcine species, the porcine species can be selected from the group consisting of a grow finish pig, a nursery pig, a sow, and a breeding stock pig. In various exemplary embodiments, the animal can be selected from the group consisting of a chicken (e.g., a broiler or a layer), a pig, a horse, a pony, a cow, a turkey, a goat, a sheep, a quail, a pheasant, an ostrich, a duck, a fish (e.g., a tilapia, a catfish, a flounder, or a salmon), a crustacean (e.g., a shrimp or a crab), and combinations thereof. In another embodiment, *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, can be used to treat a plant for plant health and can be used to treat the soil, the plant directly, or to irrigate the plant.

In any embodiments described herein, the strains can be administered in alone or in any combination, or can be in the form of any composition described herein so that the strains are alone or in any combination in the composition described herein. Exemplary combinations include a group of isolated *Bacillus* strains comprising *Bacillus* strains 101 (NRRL No. B-67218), 102 (NRRL No. B-67276), 235 (NRRL No. B-67219), 77 (NRRL No. B-67274), and 177 (NRRL No. B-67275), and a group of isolated *Bacillus* strains comprising *Bacillus* strains 101 (NRRL No. B-67218), 235 (NRRL No. B-67219), 177 (NRRL No. B-67275), and 102 (NRRL No. B-67276).

In one embodiment, a method of feeding an animal is provided. The method comprises the step of administering to the animal a feed composition or drinking water comprising an effective amount of an additive comprising an isolated *Bacillus* strain selected from the group consisting *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

In another embodiment, a method of feeding an animal is provided. The method comprises the step of administering to the animal a feed composition or drinking water comprising an effective amount of an additive comprising an isolated *Bacillus* strain selected from the group consisting *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain causes *E. coli* inhibition in the animal.

In one embodiment of the invention, an effective amount of the *Bacillus* strain can be administered to inhibit *E. coli* in the animal. As used herein, "inhibit *E. coli*" can mean reducing *E. coli* disease, preventing *E. coli* disease, maintaining the normal microbial balance in the animal, reducing the number of detrimental *E. coli* in the animal, reducing the activity of *E. coli* in the animal, or reducing the symptoms of *E. coli* disease in the animal, or combinations thereof. By "effective amount" is meant an amount of the *Bacillus* strain (e.g., strain 101, or 235, or 77, or 177, or 102) capable of *E. coli* inhibition or capable of controlling a detrimental effect of *E. coli*, as described below, by any mechanism.

In embodiments described herein wherein the compositions of the present invention comprising *Bacillus* strains 101, and/or 235, and/or 77, and/or 177, and/or 102 are administered to an animal, the compositions are preferably administered to animals orally in a feed composition or in drinking water, but any other effective method of administration known to those skilled in the art may be utilized. In one illustrative embodiment, the *Bacillus* strains 101, and/or 235, and/or 77, and/or 177, and/or 102 are provided in the form of an additive for addition to the drinking water of an animal.

In another illustrative embodiment, the *Bacillus* strains 101, and/or 235, and/or 77, and/or 177, and/or 102 are provided in the form of a feed additive for addition to a feed composition. The feed composition may contain *Bacillus* strain 101, and/or 235, and/or 77, and/or 177, and/or 102 in a mixture with an animal feed blend, including any art-recognized animal feed blend or any animal feed blend described herein. As used herein, "feed composition" or "animal feed composition" means a feed composition comprising *Bacillus* strain 101, and/or *Bacillus* strain 235, and/or *Bacillus* strain 77, and/or *Bacillus* strain 177, and/or *Bacillus* strain 102 in a mixture with an animal feed blend, and, optionally any other components that could be used in a feed composition, including other bacterial strains, such as other *Bacillus* strains or *Lactobacillus* strains.

Any animal feed blend, including those known in the art and those described herein, may be used in accordance with the methods and compositions described in this patent application, such as rapeseed meal, cottonseed meal, soybean meal, cornmeal, barley, wheat, silage, and haylage. In various embodiments, the animal feed blend can be supplemented with *Bacillus* strain 101, and/or *Bacillus* strain 235, and/or *Bacillus* strain 77, and/or *Bacillus* strain 177, and/or *Bacillus* strain 102, but other ingredients may optionally be added to the animal feed blend, including other bacterial strains, such as other *Bacillus* strains or *Lactobacillus* strains.

In various illustrative embodiments, optional ingredients of the animal feed blend include sugars and complex carbohydrates such as both water-soluble and water-insoluble monosaccharides, disaccharides, and polysaccharides. Other optional ingredients include dried distillers grain solubles, fat (e.g., crude fat), phosphorous, sodium bicarbonate, limestone, salt, phytate, calcium, sodium, sulfur, magnesium, potassium, copper, iron, manganese, zinc, ash, fish oil, an oil derived from fish meal, raw seed (e.g., flaxseed), an antioxidant, and starch. In another embodiment, minerals may be added in the form of a mineral premix.

Optional amino acid ingredients that may be added to the animal feed blend are arginine, histidine, isoleucine, leucine, lysine, cysteine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that may be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. In another embodiment, vitamins may be added in the form of a vitamin premix. In yet another embodiment, protein ingredients may be added to the animal feed blend and include protein obtained from meat meal, bone meal, or fish meal, liquid or powdered egg, fish solubles, crude protein, and the like.

In another illustrative aspect, any medicament ingredients known in the art may be added to the animal feed blend or to an additive for the drinking water of the animal, such as antibiotics. In various embodiments, the antibiotic is selected from the group consisting of ampicillin, chloramphenicol, ciprofloxacin, clindamycin, tetracycline, chlortetracycline, Denagard™, BMD™, Carbadox™, Stafac™, erythromycin, levofloxacin, trimethoprim/sulfamethoxazole, trimethoprim, daptomycin, rifampicin, Tylan™, Pulmotil™, vancomycin, and combinations thereof. In another embodiment, the animal feed blend, the feed composition, the feed additive, or the additive for the drinking water of the animal may contain no antibiotics.

In another illustrative embodiment, one or more enzymes may be added to the animal feed blend. In various embodiments, the enzymes that may be added include a galactosidase, a phytase, a protease, a lipase, an amylase, a hemicellulase, an arabinoxylanase, a xylanase, a cellulase, an NSPase, combinations thereof, and any other enzyme that improves the effectiveness of the feed composition for *E. coli* inhibition or controlling a detrimental effect of *E. coli*. In yet another embodiment, yeast, fungi (e.g., *Aspergillus* or *Trichoderma*), or micronutrients may be added to the animal feed. Any of the ingredients described above that are suitable for addition to an additive for the drinking water of the animal may be added as a component of the additive for the drinking water of the animal as described herein.

In various illustrative embodiments, the *Bacillus* strain (e.g., *Bacillus* strain 101, and/or 235, and/or 77, and/or 177, and/or 102), or any other bacterial strains added in addition to *Bacillus* strain 101, and/or 235, and/or 77, and/or 177, and/or 102, can be administered in the feed composition at a dose of about $1.0 \times 10^3$ CFU/gram of the feed composition to about $5.0 \times 10^{12}$ CFU/gram of the feed composition or at a dose of about $1.0 \times 10^3$ CFU/gram of the feed composition to about $1.0 \times 10^7$ CFU/gram of the feed composition. In other embodiments, the *Bacillus* strain (e.g., *Bacillus* strain 101, and/or 235, and/or 77, and/or 177, and/or 102) is administered in the feed composition at a dose greater than about $1.0 \times 10^3$ CFU/gram of the feed composition, at a dose greater than about $1.1 \times 10^3$ CFU/gram of the feed composition, at a dose greater than about $1.25 \times 10^3$ CFU/gram of the feed composition, at a dose greater than about $1.5 \times 10^3$ CFU/gram of the feed composition, at a dose greater than about $1.75 \times 10^3$ CFU/gram of the feed composition, at a dose greater than about $1.0 \times 10^4$ CFU/gram of the feed composition, at a dose greater than about $2.0 \times 10^4$ CFU/gram of the feed composition, at a dose greater than about $3.0 \times 10^4$ CFU/gram of the feed composition, at a dose greater than about $4.0 \times 10^4$ CFU/gram of the feed composition, at a dose greater than about $5.0 \times 10^4$ CFU/gram of the feed composition, at a dose greater than about $6.0 \times 10^4$ CFU/gram of the feed composition, at a dose greater than about $7.0 \times 10^4$ CFU/gram of the feed composition, at a dose greater than about $8.0 \times 10^4$ CFU/gram of the feed composition, at a dose greater than about $1.0 \times 10^5$ CFU/gram of the feed composition, at a dose greater than about $1.0 \times 10^6$ CFU/gram of the feed composition, at a dose greater than about $1.0 \times 10^7$ CFU/gram of the feed composition, at a dose greater than about $1.0 \times 10^8$ CFU/gram of the feed composition, at a dose greater than about $1.0 \times 10^9$ CFU/gram of the feed composition, at a dose greater than about $1.0 \times 10^{10}$ CFU/gram of the feed composition, at a dose greater than about $1.0 \times 10^{11}$ CFU/gram of the feed composition, or at a dose greater than about $1.0 \times 10^{12}$ CFU/gram of the feed composition. In yet another embodiment, the *Bacillus* strain (e.g., *Bacillus* strain 101, and/or 235, and/or 77, and/or 177, and/or 102) is administered in the feed composition at a dose of about $7.3 \times 10^4$ CFU/gram of the feed composition. In another embodiment, the *Bacillus* strain (e.g., *Bacillus* strain 101, and/or 235, and/or 77, and/or 177, and/or 102), or any other bacterial strains added in addition to *Bacillus* strain 101, and/or 235, and/or 77, and/or 177, and/or 102, can be administered in the feed composition at a dose of about $1.0 \times 10^2$ CFU/gram of the feed composition to about $5.0 \times 10^{12}$ CFU/gram of the feed composition or at a dose of about $1.0 \times 10^2$ CFU/gram of the feed composition to about $1.0 \times 10^7$ CFU/gram of the feed composition, or at a dose greater than about $1.0 \times 10^2$ CFU/gram of the feed composition.

In various embodiments, the *Bacillus* strain (e.g., *Bacillus* strain 101, and/or 235, and/or 77, and/or 177, and/or 102) for use in accordance with the methods and compositions described herein can be selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), and a strain having all of the identifying characteristics of *Bacillus* strain 102 (NRRL No. B-67276). *Bacillus* strain MDG 101 and *Bacillus* strain MDG 235 were deposited on Jan. 4, 2016 at the Agricultural Research Service Culture Collection (NRRL), National Center for Agricultural Utilization Research, Agricultural Research Service, USDA, 1815 North University Street, Peoria, Ill. 61604-3999, and were given accession numbers B-67218 and B-67219, respectively. *Bacillus* strain MGL77, *Bacillus* strain MGL177, and *Bacillus* strain MGL102 were deposited on Jun. 7, 2016 at the Agricultural Research Service Culture Collection (NRRL), National Center for Agricultural Utilization Research, Agricultural Research Service, USDA, 1815 North University Street, Peoria, Ill. 61604-3999, and were given accession numbers B-67274, B-67275, and B-67276, respectively. The deposits were made under the provisions of the Budapest Treaty on the International Recognition of the Deposit of Microorganisms for the Purposes of Patent Procedure. The NRRL strain designations are MDG 101, MDG 235, MGL77, MGL177, and MGL102 which are equivalent to *Bacillus* strain 101, 235, 77, 177, and 102 respectively, as referred to in the application.

Any of these strains can be administered alone or in combination in the form of a feed composition (e.g., a complete feed comprising an animal feed blend) or drinking water for an animal. In one embodiment, multiple strains are administered in combination in a single composition. In another embodiment, multiple strains are administered in combination in separate compositions. In one illustrative embodiment, any of these strains is isolated from a high performing grow finish pig.

In another embodiment, one or more of the *Bacillus* strains described in the preceding paragraphs (e.g., *Bacillus* strain 101, and/or *Bacillus* strain 235, and/or *Bacillus* strain 77, and/or *Bacillus* strain 177, and/or *Bacillus* strain 102) can be administered to the animal along with another bacterial strain selected from the group consisting of another *Bacillus* strain, a lactic acid bacterial strain, and combinations thereof. In yet another embodiment, one or more of the *Bacillus* strains described in the preceding paragraphs (e.g., *Bacillus* strain 101, and/or *Bacillus* strain 235, and/or *Bacillus* strain 77, and/or *Bacillus* strain 177, and/or *Bacillus* strain 102) can be administered to the animal along with any other bacterial strain effective to inhibit *E. coli* in the animal.

As used herein "a strain having all of the identifying characteristics of" *Bacillus* strain 101, or *Bacillus* strain 235, or *Bacillus* strain 77, or *Bacillus* strain 177, or *Bacillus* strain 102 can be a mutant strain having all of the identifying characteristics of *Bacillus* strain 101, or *Bacillus* strain 235, or *Bacillus* strain 77, or *Bacillus* strain 177, or *Bacillus* strain 102 (e.g., a DNA fingerprint based on DNA analysis that corresponds to the DNA fingerprint of *Bacillus* strain 101, or *Bacillus* strain 235, or *Bacillus* strain 77, or *Bacillus* strain 177, or *Bacillus* strain 102, enzyme activities that correspond to *Bacillus* strain 101, or *Bacillus* strain 235, or *Bacillus* strain 77, or *Bacillus* strain 177, or *Bacillus* strain 102, antimicrobial activity that corresponds to *Bacillus* strain 101, or *Bacillus* strain 235, or *Bacillus* strain or 77, *Bacillus* strain or 177, or *Bacillus* strain 102, antibiotic sensitivity and tolerance profiles that correspond to *Bacillus* strain 101, or *Bacillus* strain 235, or *Bacillus* strain 77, or *Bacillus* strain 177, or *Bacillus* strain 102, or combinations thereof). In alternate embodiments, the mutation can be a natural mutation, or a genetically engineered mutation. In another embodiment, "a strain having all of the identifying characteristics of" *Bacillus* strain 101, or *Bacillus* strain 235, or *Bacillus* strain 77, or *Bacillus* strain 177, or *Bacillus* strain 102 can be a strain, for example, produced by isolating one or more plasmids from *Bacillus* strain 101, or *Bacillus* strain 235, or *Bacillus* strain 77, or *Bacillus* strain 177, or *Bacillus* strain 102 and introducing the one or more plasmids into another bacterium, such as another *Bacillus* strain, as long as the one or more plasmids contain DNA that provides the identifying characteristics of *Bacillus* strain 101, or *Bacillus* strain 235, or *Bacillus* strain 77, or *Bacillus* strain 177, or *Bacillus* strain 102 (e.g., a DNA fingerprint based on DNA analysis that corresponds to the DNA fingerprint of *Bacillus* strain 101, or *Bacillus* strain 235, or *Bacillus* strain 77, or *Bacillus* strain 177, or *Bacillus* strain 102).

The feed composition or drinking water comprising *Bacillus* strain 101, and/or 235, and/or 77, and/or 177, and/or 102 may be administered to the animal for any time period that is effective to inhibit *E. coli* or control a detrimental effect of *E. coli*, or combinations thereof. For example, in one embodiment the feed composition or drinking water may be provided to the animal daily. In an alternate embodiment, the feed composition or drinking water may be administered to the animal during lactation and/or during gestation. The time periods for administration of the feed composition or drinking water described above are non-limiting examples and it should be appreciated that any time period or administration schedule determined to be effective to inhibit *E. coli* or control a detrimental effect of *E. coli*, or combinations thereof, may be used.

As described herein, one of the method embodiments is a method of feeding an animal by administering to the animal a feed composition or drinking water comprising an effective amount of an additive comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain controls a detrimental effect of *E. coli*. Any of the applicable above-described embodiments can apply to this embodiment.

In this embodiment, "controlling a detrimental effect of *E. coli*" can mean reducing *E. coli* disease, preventing *E. coli* disease, maintaining the normal microbial balance in the animal, reducing the number of detrimental *E. coli* in the animal, reducing the activity of *E. coli* in the animal, or reducing the symptoms of *E. coli* disease in the animal, or combinations thereof. By "effective amount" is meant an amount of the *Bacillus* strain (e.g., strain 101, or 235, or 77, or 177, or 102) capable of controlling a detrimental effect of *E. coli*, as described above, by any mechanism.

In additional embodiments of the invention, compositions comprising *Bacillus* strain 101, and/or *Bacillus* strain 235, and/or *Bacillus* strain 77, and/or *Bacillus* strain 177, and/or *Bacillus* strain 102 are provided. In one embodiment, a commercial package is provided comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

In another embodiment, a feed additive for an animal feed is provided comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

In yet another embodiment, an additive for the drinking water of an animal is provided comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

In yet another illustrative aspect of the invention, an animal feed composition is provided comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof.

In another embodiment an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof can be used in maintaining plant health, aquaculture, or for use in food processing.

In one embodiment, the feed additive for addition to an animal feed blend to produce a complete feed composition can be mixed with the animal feed blend, for example, with an automated micro-nutrient delivery system, or, for example, by hand-weighing and addition to achieve any of the doses of *Bacillus* strain 101, *Bacillus* strain 235, *Bacillus* strain 77, *Bacillus* strain 177, and *Bacillus* strain 102 described herein, for administration to the animal in the form of a complete feed composition. The mixing can also be done by any other suitable method known in the art for combining direct-fed microbials with an animal feed blend to obtain a uniform mixture. In various embodiments, the mixing can be done for any suitable time period (e.g., about 1 to about 4 minutes). In the embodiment where *Bacillus* strain 101, and/or *Bacillus* strain 235, and/or *Bacillus* strain 77, and/or *Bacillus* strain 177, and/or *Bacillus* strain 102 is in the form of an additive for the drinking water of the animal, the *Bacillus* strain 101, and/or *Bacillus* strain 235, and/or *Bacillus* strain 77, and/or *Bacillus* strain 177, and/or *Bacillus* strain 102 can be in the form of, for example, a powder, a liquid, or pellets, and can be mixed with the drinking water using any suitable method known in the art to achieve any of the doses of *Bacillus* strain 101, *Bacillus* strain 235, *Bacillus* strain 77, *Bacillus* strain 177, or *Bacillus* strain 102 described herein, for administration to the animal in the drinking water of the animal. *Bacillus* strain 101, and/or *Bacillus* strain 235, and/or *Bacillus* strain 77, and/or *Bacillus* strain 177, and/or *Bacillus* strain 102 can also be fed directly to the animal orally (i.e., by oral insertion) in the form of a powder, a liquid, or a pellet.

In any of the composition embodiments described herein, the *Bacillus* strain 101, and/or *Bacillus* strain 235, and/or *Bacillus* strain 77, and/or *Bacillus* strain 177, and/or *Bacillus* strain 102 can cause an effect selected from the group consisting of inhibiting *E. coli* or controlling a detrimental effect of *E. coli* in the animal. These effects are non-limiting examples of the types of effects *Bacillus* strain 101, and/or *Bacillus* strain 235, and/or *Bacillus* strain 77, and/or *Bacillus* strain 177, and/or *Bacillus* strain 102 can cause.

In one illustrative aspect, the feed additive, additive for the drinking water of the animal, or the feed composition can be in the form of a commercial package. In another illustrative embodiment, the feed additive or additive for the drinking water of the animal, or the *Bacillus* strain 101, and/or *Bacillus* strain 235, and/or *Bacillus* strain 77, and/or *Bacillus* strain 177, and/or *Bacillus* strain 102 in the commercial package can be in the form of a concentrate (e.g., about $1 \times 10^8$ to about $5 \times 10^9$ CFU/g) or a super concentrate (e.g., about $1 \times 10^{10}$ to about $5 \times 10^{12}$ CFU/g). In another embodiment, the feed additive, feed composition, or additive for the drinking water of the animal, or the *Bacillus* strain 101, and/or *Bacillus* strain 235, and/or *Bacillus* strain 77, and/or *Bacillus* strain 177, and/or *Bacillus* strain 102 in a composition in a commercial package, can be in a dry form (e.g., a powder), a pelleted form, a liquid form, in the form of a top-dressing, or in the form of a gel, or any other suitable form.

In yet another embodiment, the strains in the form of a commercial package can be, for example, in a dry form (e.g., a powder or freeze-dried form), in a pelleted form, or in a liquid form.

In another illustrative embodiment, the commercial package, feed additive, additive for the drinking water of the animal, or feed composition can further comprise a carrier for the *Bacillus* strain 101, and/or *Bacillus* strain 235, and/or *Bacillus* strain 77, and/or *Bacillus* strain 177, and/or *Bacillus* strain 102. The carrier can be selected from the group consisting of a bran, rice hulls, a salt, mineral oil, a dextrin (e.g., maltodextrin), whey, sugar, limestone, dried starch, sodium silico aluminate, vegetable oil, and combinations thereof. In another embodiment, the carrier can be any suitable carrier known in the art for a direct-fed microbial. In another embodiment, the commercial package, feed additive, additive for the drinking water of the animal, or feed composition can further comprise a binder such as clay, yeast cell wall components, aluminum silicate, glucan, or other known binders. In another embodiment, the commercial package, feed additive, additive for the drinking water of the animal, or feed composition can further comprise inorganic/organic binders, essential oils, and/or organic acids.

In yet other embodiments, the commercial package, feed additive, additive for the drinking water of the animal, or feed composition comprising *Bacillus* strain 101, and/or *Bacillus* strain 235, and/or *Bacillus* strain 77, and/or *Bacillus* strain 177, and/or *Bacillus* strain 102 is in a container for commercial use. In various embodiments the container can be, for example, a bag (e.g., a 20-pound bag, a 50-pound bag, a 2-ounce bag, a 1-pound bag, or a 1-kilogram bag), a pouch, a drum, a bottle, or a box. In illustrative aspects, the container for the commercial package, feed additive, additive for the drinking water of the animal, or feed composition comprising *Bacillus* strain 101, and/or *Bacillus* strain 235, and/or *Bacillus* strain 77, and/or *Bacillus* strain 177, and/or *Bacillus* strain 102 can comprise plastic, metal, foil, paper, fiber, or cardboard (e.g., a plastic pail, a paper bag, a foil bag, a fiber drum, etc.). The commercial package, feed additive, additive for the drinking water of the animal, or feed composition can further comprise instructions for use of one or more of the *Bacillus* strains.

The following examples are for illustrative purposes only. The examples are non-limiting, and are not intended to limit the invention in any way.

EXAMPLE 1

Enzymatic Activity Screening

This example describes the use of plate media screening methods to detect enzymatic activity in DFM strains 101 and 235. Enzyme assay media plates were prepared by supplementing tryptic soy agar with between 0.5% and 1% of various substrates, including polysaccharides (corn starch, carboxymethylcellulose, or xylan), proteins (casein), and lipids (tributyrin). *Bacillus* strains of interest (including DFM strains 101 and 235) obtained from fresh overnight cultures were spotted onto plates (5 µL) and incubated at various temperatures for up to 48 hours. For protein and lipid agar plates, zones of clearing around enzyme-producing colonies were visible without further treatment. Polysaccharide-containing plates were stained with Gram's iodine for 1 minute to visualize zones of clearing. ZOC diameters and colony diameters were measured, but yes/no scores of activity were used for screening purposes. DFM strains 101 and 235 were both observed to be positive for protease, amylase, and xylanase activity after 48 hours and strong positives on tributyrin agar (lipase) were observed.

The *Bacillus* strains described herein have enzymatic activity including but not limited to amylase, protease, xylanase and lipase.

EXAMPLE 2

Antimicrobial Screening with the Cross-Streak Method

For facultative anaerobic pathogens tested (*E. coli*) the following protocol was used. *Bacillus* strains of interest (101 and 235) were inoculated from frozen glycerol stocks in a single 1 cm wide linear streak down the center of modified BHI agar plates. *Bacillus*-streaked plates were inoculated aerobically for 24 hours at 37° C., until a heavy streak of growth was present. The organism to be tested for susceptibility, *E. coli*, was streaked in lines perpendicular towards the *Bacillus* streak (up to 1 mm) in a biological safety cabinet and incubated at 37° C. for 24 hours under aerobic conditions. No more than 5 staggered cross streaks per plate were used. The plates were incubated and then examined for zones of inhibition around the initial *Bacillus* streak, and the width of each zone of inhibition was measured in millimeters. MDG strains 101 and 235 consistently inhibited *E. coli*. To date, 58 different pathogenic *E. coli* strains were tested for susceptibility to strains 101 and 43 different strains for susceptibility to 235. These strains vary numerous characteristics including toxin presence and quantity, colony morphology on SMAC agar, hemolysin production, and specimen location around the U.S. Strain 101 successfully inhibited 46 of 58 *E. coli* isolates when it was grown both aerobically and anaerobically while strain 235 successfully inhibited 42 of 43 *E. coli* isolates when grown both aerobically and anaerobically.

EXAMPLE 3

Culture Growth of DFM Strains 101 and 235

In the instant example, growth of DFM strains 101 and 235 can be achieved by culturing. On a small scale, TSB or nutrient broth can be utilized to culture DFM strains 101 and 235.

Agar medium may be produced using 23 grams Nutrient Agar (BD 213000) and 1000 ml of DI water, followed by autoclaving at 121° C. Broth medium may be produced using 8.0 grams of Nutrient Broth (BD 234000) and 1000 ml of DI water, followed by autoclaving at 121° C.

For culturing DFM strain 101, a pure culture of DFM strain 101 was streaked on a nutrient agar plate and allowed to grow for 48 hours at 32° C. Thereafter, a single colony was inoculated in nutrient broth medium. The single colony was incubated at 37° C. and at 230-240 rpm, for 16 to 24 hours. Finally, the culture was streaked on a nutrient agar plate to check morphology.

For culturing DFM strain 235, a pure culture of DFM strain 235 was streaked on a nutrient agar plate and allowed to grow for 48 hours at 32° C. Thereafter, a single colony was inoculated in nutrient broth medium. The single colony was incubated at 37° C. and at 230-240 rpm, for 16 to 24 hours. Finally, the culture was streaked on a nutrient agar plate to check morphology.

EXAMPLE 4

Antimicrobial Screening with the Cross-Streak Method

For *E. coli* tested, the protocol described in Example 2 was used. MGL strains 77, 177, and 102 consistently inhibited *E. coli*. To date, 15 different pathogenic *E. coli* strains were tested for susceptibility to strains 77, 177, and 102. Strain 77 successfully inhibited 11 of 15 *E. coli* isolates when it was grown aerobically, strain 177 successfully inhibited 12 of 15 *E. coli* isolates when it was grown aerobically, and strain 102 successfully inhibited 15 of 15 *E. coli* isolates when it was grown aerobically (see Table 1 below).

TABLE 1

|  | 102 | 77 | 177 |
|---|---|---|---|
| K1.8 (Beta) | + | + | + |
| K 2.4 (beta) | + | + | − |
| K2.5 (beta) | + | + | + |
| J 2.5 (beta) | + | + | + |
| K1.7 (beta) | + | + | + |
| K1.9 (beta) | + | − | + |
| K1.10 (beta) | + | − | − |
| K2.8 (beta) | + | + | + |
| K1.8 (beta) | + | + | + |
| J 1.2 (beta) | + | − | − |
| 1A (α) | + | − | + |
| 1B (α) | + | + | + |
| 1C (α) | + | + | + |
| 1D (α) | + | + | + |
| 1E (α) | + | + | + |

What is claimed is:

1. A nutrient composition comprising an isolated *Bacillus* strain selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), *Bacillus* strain 102 (NRRL No. B-67276), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 77 (NRRL No. B-67274), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the composition further comprises a carrier and the composition causes *E. coli* inhibition in an animal.

2. The composition of claim 1 wherein the carrier is selected from the group consisting of a bran, rice hulls, a salt, mineral oil, a dextrin, whey, sugar, limestone, dried starch, sodium silico aluminate, vegetable oil, and combinations thereof.

3. The composition of claim 1 wherein the composition further comprises an exogenously added nutrient component selected from the group consisting of a vitamin, an antibiotic, an enzyme, a water-soluble or water-insoluble monosaccharide, disaccharide, or polysaccharide, a fat, phosphorous, sodium bicarbonate, limestone, calcium, sodium, sulfur, magnesium, potassium, copper, iron, manganese, zinc, fish oil, raw seed, an antioxidant, and a starch.

4. The composition of claim 1 further comprising a binder wherein the binder is selected from the group consisting of clay, yeast cell wall components, aluminum silicate, glucan, and combinations thereof.

5. The composition of claim 1 in the form of a commercial package.

6. The composition of claim 5 wherein the commercial package comprises a container selected from the group consisting of a bag, a pouch, a drum, a bottle, and a box.

7. The composition of claim 3 wherein the exogenously added component is an enzyme.

8. The composition of claim 7 wherein the enzyme is selected from the group consisting of a galactosidase, a protease, a lipase, an amylase, a hemicellulase, an arabinoxylanase, a xylanase, a cellulase, an NSPase, a phytase, and combinations thereof.

9. The composition of claim 1 wherein the isolated *Bacillus* strain is selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), and *Bacillus* strain 102 (NRRL No. B-67276), and combinations thereof.

10. The composition of claim 2 wherein the isolated *Bacillus* strain is selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), and *Bacillus* strain 102 (NRRL No. B-67276), and combinations thereof.

11. The composition of claim 3 wherein the isolated *Bacillus* strain is selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), and *Bacillus* strain 102 (NRRL No. B-67276), and combinations thereof.

12. The composition of claim 4 wherein the isolated *Bacillus* strain is selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), and *Bacillus* strain 102 (NRRL No. B-67276), and combinations thereof.

13. The composition of claim 5 wherein the isolated *Bacillus* strain is selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), and *Bacillus* strain 102 (NRRL No. B-67276), and combinations thereof.

14. The composition of claim 6 wherein the isolated *Bacillus* strain is selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), and *Bacillus* strain 102 (NRRL No. B-67276), and combinations thereof.

15. The composition of claim 7 wherein the isolated *Bacillus* strain is selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), and *Bacillus* strain 102 (NRRL No. B-67276), and combinations thereof.

16. The composition of claim 8 wherein the isolated *Bacillus* strain is selected from the group consisting of *Bacillus* strain 101 (NRRL No. B-67218), *Bacillus* strain 235 (NRRL No. B-67219), *Bacillus* strain 77 (NRRL No. B-67274), *Bacillus* strain 177 (NRRL No. B-67275), and *Bacillus* strain 102 (NRRL No. B-67276), and combinations thereof.

* * * * *